(12) United States Patent
Singer et al.

(10) Patent No.: US 9,839,590 B2
(45) Date of Patent: Dec. 12, 2017

(54) METHODS AND COMPOSITIONS FOR IMPROVING THE QUALITY AND DURABILITY OF COLOR IN ARTIFICIALLY COLORED HAIR

(71) Applicant: L'OREAL, Paris (FR)

(72) Inventors: Jim Singer, South Orange, NJ (US); Nghi Van Nguyen, Edison, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/153,084

(22) Filed: May 12, 2016

(65) Prior Publication Data

US 2017/0326050 A1    Nov. 16, 2017

(51) Int. Cl.
*A61Q 5/10* (2006.01)
*A61K 8/365* (2006.01)
*A61K 8/20* (2006.01)

(52) U.S. Cl.
CPC ............... *A61K 8/365* (2013.01); *A61K 8/20* (2013.01); *A61Q 5/10* (2013.01); *A61K 2800/4324* (2013.01); *A61K 2800/884* (2013.01)

(58) Field of Classification Search
CPC ..... A61Q 5/10; A61K 8/365; A61K 2800/884
See application file for complete search history.

(56) References Cited

U.S. PATENT DOCUMENTS

| | | | |
|---|---|---|---|
| 5,006,127 | A | 4/1991 | Tennigkeit et al. |
| 5,635,168 | A | 6/1997 | Burns et al. |
| 6,569,412 | B2 | 5/2003 | Yamaguchi et al. |
| 7,713,310 | B2 | 5/2010 | Lalleman |
| 8,002,849 | B2 | 8/2011 | Prem et al. |
| 2001/0007160 | A1 | 7/2001 | Yamaguchi et al. |
| 2002/0189031 | A1 | 12/2002 | Javet et al. |
| 2004/0158940 | A1 | 8/2004 | Wells et al. |
| 2005/0098763 | A1 | 5/2005 | Plos et al. |
| 2005/0142090 | A1 | 6/2005 | Watanabe |
| 2005/0198747 | A1 | 9/2005 | Emmerling et al. |
| 2008/0260672 | A1 | 10/2008 | Oshimura et al. |
| 2010/0068164 | A1* | 3/2010 | Verboom ............... A61K 8/416 424/70.9 |
| 2010/0242982 | A1 | 9/2010 | Prem et al. |
| 2010/0254924 | A1* | 10/2010 | Hamilton ............... A61K 8/342 424/62 |
| 2011/0044924 | A1* | 2/2011 | Verboom ............... A61K 8/416 424/70.9 |
| 2015/0050229 | A1 | 2/2015 | Krueger |
| 2015/0265525 | A1 | 9/2015 | Benn et al. |

FOREIGN PATENT DOCUMENTS

| | | |
|---|---|---|
| DE | 102005062360 A1 | 6/2007 |
| FR | 3004944 A1 | 10/2014 |
| WO | WO-2014/203771 A1 | 12/2014 |

OTHER PUBLICATIONS

STIC Search Report dated Sep. 16, 2016.*
International Search Report dated Aug. 4, 2017 for corresponding Application No. PCT/US17/32140.

* cited by examiner

*Primary Examiner* — Eisa Elhilo
(74) *Attorney, Agent, or Firm* — Polsinelli PC

(57) ABSTRACT

The present disclosure relates to compositions and methods for improving the quality and durability of color in artificially colored hair. The methods employ alkaline earth metal salts that act as a mordant (a fixing agent) with hair dye and salts of hydroxy-polycarboxylic acids, which act as chelators. Methods are described wherein the alkaline earth metal salts or the salts of hydroxy-polycarboxylic acids are used in a pre-color treatment (a treatment to the hair prior to artificial coloring), used as part of a coloring composition, and used in a post-color treatment (a treatment to the hair after artificial coloring).

19 Claims, No Drawings

METHODS AND COMPOSITIONS FOR IMPROVING THE QUALITY AND DURABILITY OF COLOR IN ARTIFICIALLY COLORED HAIR

FIELD OF THE DISCLOSURE

The present disclosure relates to compositions and methods for providing color protection to hair, in particular, for improving the quality and durability of color in artificially colored hair. The methods employ alkaline earth metal salts that act as a mordant (a fixing agent) with dyes, and salts of hydroxy-polycarboxylic acids, which act as chelators.

BACKGROUND

There are many products available for changing the natural color of hair. The process of changing the color of hair can involve either depositing an artificial color onto the hair, which provides a different shade or color to the hair, or lifting the color of the hair, such as for example, from a dark brown shade to a medium brown or a light brown shade. Hair color can be changed using permanent, semi-permanent, or temporary hair coloring products.

Many consumers desire a permanent color change and therefore use products containing permanent dyes. Conventional permanent hair coloring products are dye compositions comprising oxidation dye precursors, which are also known as primary intermediates or couplers. These oxidation dye precursors are colorless or weakly colored compounds which, when combined with oxidizing products, give rise to colored complexes by a process of oxidative condensation. The oxidizing products conventionally use peroxides such as hydrogen peroxide as oxidizing agents. Such permanent hair color products also contain ammonia or other alkalizing agents such as monoethanolamine (MEA) which causes the hair shaft to swell, thus allowing the small oxidative dye molecules to penetrate the cuticle and cortex before the oxidation condensation process is completed. The resulting larger-sized colored complexes from the oxidative reaction are then trapped inside the hair fiber, thereby permanently altering the color of the hair.

Newly, permanently colored hair usually has a vibrant, shiny, and rich appearance. Unfortunately, however, in just a few short weeks, or in some cases even less, the color begins to fade due to washing or exposure to environmental conditions. For instance, gorgeous rich brown colors become muddy and dull, beautiful shades of blonde turn brassy, and vibrant reds do not look so vibrant anymore acquiring golden, orange or brownish tonalities not desirable to the consumer. As described herein, the inventors of the instant disclosure have developed methods and kits that improve color durability by preventing color fading from hair.

SUMMARY OF THE DISCLOSURE

The present disclosure relates to improving the quality and durability of the color in artificially colored hair. The methods described herein employ alkaline earth metal salts that act as a mordant (a fixing agent) with hair dye and salts of hydroxy-polycarboxylic acids, which act as chelators. When both of these components are used in the methods described herein, color quality and color durability are improved.

In one aspect, methods for artificially coloring hair and inhibiting the coloring from fading involve: (a) treating hair with a pre-color treatment composition comprising one or more alkaline earth metal salts or one or more salts of a hydroxy-polycarboxylic acid, wherein hydroxy-polycarboxylic acid has the formula:

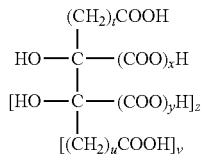

wherein, x and y are independently 0 or 1; and
t, u, v, and z are independently 0 to 3; and
(b) treating the hair with a coloring composition comprising the one or more alkaline earth metal salts or the one or more salts of a hydroxy-polycarboxylic acid; provided that when the one or more alkaline earth metal salts is used in the pre-color treatment composition, the one or more salts of the hydroxy-polycarboxylic acid is used in the coloring composition, and vice versa.

In another aspect, methods for artificially coloring hair and inhibiting the coloring from fading involve: (a) treating hair with a pre-color treatment composition comprising one or more alkaline earth metal salts or one or more salts of a hydroxy-polycarboxylic acid of the formula

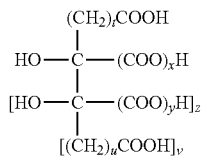

wherein, x and y are independently 0 or 1; and
t, u, v, and z are independently 0 to 3; and
(b) treating the hair with a coloring composition; and (c) treating the hair with a post-color treatment composition comprising the one or more alkaline earth metal salts or the one or more salts of a hydroxy-polycarboxylic acid; provided that when the one or more alkaline earth metal salts is used in the pre-color treatment composition, the one or more salts of the hydroxy-polycarboxylic acid is used in the post-color treatment composition, and vice versa.

In yet another aspect, methods for artificially coloring hair and inhibiting the coloring from fading involve: (a) treating the hair with a coloring composition comprising one or more alkaline earth metal salts one or more salts of a hydroxy-polycarboxylic acid, wherein hydroxy-polycarboxylic acid has the formula:

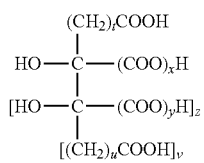

wherein, x and y are independently 0 or 1; and
t, u, v, and z are independently 0 to 3; and
(b) treating the hair with a post-color treatment composition comprising the one or more alkaline earth metal salts or the one or more salts of a hydroxy-polycarboxylic acid;

provided that when the one or more alkaline earth metal salts is used in the coloring composition, the one or more salts of the hydroxy-polycarboxylic acid is used in the post-color treatment composition, and vice versa.

The one or more salts of the hydroxy-polycarboxylic acid are typically alkali metal salts, alkaline earth metal salts, and/or transition metal salts. Non-limiting examples of salts of the hydroxy-polycarboxylic acid include salts of citric acid, tartaric acid, malic acid, 2-hydroxy malonic acid, 2-hydroxyl n-butyl 1,2,4-tricarboxylic acid, glucaric acid, and/or 2-hydroxy n-butyl 1,3,4-tricarboxylic acid.

Non-limiting examples of alkaline earth metal salts include magnesium chloride, magnesium sulfate, magnesium nitrate, magnesium acetate, magnesium carbonate and hydrogencarbonate, magnesium phosphate, magnesium oxalate, calcium chloride, calcium nitrate, calcium acetate, calcium hydrogen carbonate strontium chloride, strontium nitrate, barium chloride, and barium nitrate.

Finally, the instant disclosure relates to kits comprising the various compositions used to carry out the methods described herein. The kits may be used by hair-care professionals and salons for treating the hair of patrons or the kits may be purchased and used at home directly by consumers.

DETAILED DESCRIPTION OF THE DISCLOSURE

Alkaline earth metal salts and salts of hydroxy-polycarboxylic acids can be used in pre-color treatment, in coloring treatment, and in post-color treatment compositions to improve the quality of hair color and to prevent the color from fading. In one aspect, methods for artificially coloring hair and inhibiting the coloring from fading involve: (a) treating hair with a pre-color treatment composition comprising about 1 wt. % to about 75 wt. % of one or more alkaline earth metal salts or about 1 wt. % to about 75 wt. % of one or more salts of a hydroxy-polycarboxylic acid, wherein hydroxy-polycarboxylic acid has the formula:

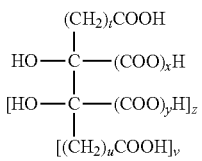

wherein, x and y are independently 0 or 1; and t, u, v, and z are independently 0 to 3; and (b) treating the hair with a coloring composition comprising about 1 wt. % to about 50 wt. % of the one or more alkaline earth metal salts or about 1 wt. % to about 50 wt. % of the one or more salts of a hydroxy-polycarboxylic acid; provided that when the one or more alkaline earth metal salts is used in the pre-color treatment composition, the one or more salts of the hydroxy-polycarboxylic acid is used in the coloring composition, and vice versa.

In another aspect, methods for artificially coloring hair and inhibiting the coloring from fading involve: (a) treating hair with a pre-color treatment composition comprising about 1 wt. % to about 75 wt. % of one or more alkaline earth metal salts or about 1 wt. % to about 75 wt. % of one or more salts of a hydroxy-polycarboxylic acid of the formula

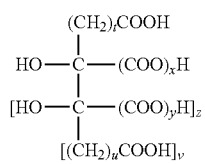

wherein, x and y are independently 0 or 1; and t, u, v, and z are independently 0 to 3; and (b) treating the hair with a coloring composition; and (c) treating the hair with a post-color treatment composition comprising about 1 wt. % to about 75 wt. % of the one or more alkaline earth metal salts or about 1 wt. % to about 75 wt. % of the one or more salts of a hydroxy-polycarboxylic acid; provided that when the one or more alkaline earth metal salts is used in the pre-color treatment composition, the one or more salts of the hydroxy-polycarboxylic acid is used in the post-color treatment compositions, and vice versa.

In yet another aspect, methods for artificially coloring hair and inhibiting the coloring from fading involve: (a) treating the hair with a coloring composition comprising about 1 wt. % to about 50 wt. % of one or more alkaline earth metal salts or about 1 wt. % to about 50 wt. % of one or more salts of a hydroxy-polycarboxylic acid, wherein hydroxy-polycarboxylic acid has the formula:

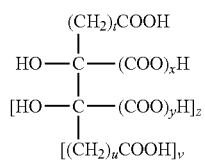

wherein, x and y are independently 0 or 1; and t, u, v, and z are independently 0 to 3; and (b) treating the hair with a post-color treatment composition comprising about 1 wt. % to about 75 wt. % of the one or more alkaline earth metal salts or about 1 wt. % to about 75 wt. % of the one or more salts of a hydroxy-polycarboxylic acid; provided that when the one or more alkaline earth metal salts is used in the coloring composition, the one or more salts of the hydroxy-polycarboxylic acid is used in the post-color treatment composition, and vice versa.

The one or more salts of the hydroxy-polycarboxylic acid are typically alkali metal salts, alkaline earth metal salts, and/or transition metal salts. Non-limiting examples of salts of the hydroxy-polycarboxylic acid include salts of citric acid, tartaric acid, malic acid, 2-hydroxy malonic acid, 2-hydroxyl n-butyl 1,2,4-tricarboxylic acid, glucaric acid, and/or 2-hydroxy n-butyl 1,3,4-tricarboxylic acid. In some cases, sodium citrate salts are used, such as trisodium citrate.

Non-limiting examples of alkaline earth metal salts include magnesium chloride, magnesium sulfate, magnesium nitrate, magnesium acetate, magnesium carbonate and hydrogencarbonate, magnesium phosphate, magnesium oxalate, calcium chloride, calcium nitrate, calcium acetate, calcium hydrogen carbonate strontium chloride, strontium nitrate, barium chloride, and barium nitrate. In some cases, calcium chloride is used.

The total amount of the one or more salts of the hydroxy-polycarboxylic acid or the one or more alkaline earth metal salts, when used in a pre-color treatment composition, is about 1 wt. % to about 75 wt. %, based on the total weight of the pre-color treatment composition. The total amount of the one more salts may be from about 1 wt. % to about 25 wt. %, about 30 wt. %, about 35 wt. %, about 40 wt. %, about 45 wt. %, about 50 wt. %, about 55 wt. %, about 60 wt. %, about 65 wt. %, or about 70 wt. %. The total amount of the one more salts may be from about 5 wt. % to about 25 wt. %, about 30 wt. %, about 35 wt. %, about 40 wt. %, about 45 wt. %, about 50 wt. %, about 55 wt. %, about 60 wt. %, about 65 wt. %, or about 70 wt. %. The total amount of the one more salts may be from about 10 wt. % to about 25 wt. %, about 30 wt. %, about 35 wt. %, about 40 wt. %, about 45 wt. %, about 50 wt. %, about 55 wt. %, about 60 wt. %, about 65 wt. %, or about 70 wt. %. The total amount of the one more salts may be from about 15 wt. % to about 25 wt. %, about 30 wt. %, about 35 wt. %, about 40 wt. %, about 45 wt. %, about 50 wt. %, about 55 wt. %, about 60 wt. %, about 65 wt. %, or about 70 wt. %. The total amount of the one more salts may be from about 20 wt. % to about 40 wt. %, about 45 wt. %, about 50 wt. %, about 55 wt. %, about 60 wt. %, about 65 wt. %, or about 70 wt. %. The total amount of the one more salts may be from about 25 wt. % to about 40 wt. %, about 45 wt. %, about 50 wt. %, about 55 wt. %, about 60 wt. %, about 65 wt. %, or about 70 wt. %. The total amount of the one more salts may be from about 30 wt. % to about 45 wt. %, about 50 wt. %, about 55 wt. %, about 60 wt. %, about 65 wt. %, or about 70 wt. %.

The total amount of the one or more salts of the hydroxy-polycarboxylic acid or the one or more alkaline earth metal salts, when used in a coloring composition, is about 1 wt. % to about 50 wt. %, based on the total weight of the coloring composition. The total amount of the one or more salts may be from about 1 wt. % to about 15 wt. %, about 20 wt. %, about 25 wt. %, about 30 wt. %, about 35 wt. %, about 40 wt. %, about 45 wt. %, or about 50 wt. %. The total amount of the one or more salts may be from about 5 wt. % to about 20 wt. %, about 25 wt. %, about 30 wt. %, about 35 wt. %, about 40 wt. %, about 45 wt. %, or about 50 wt. %. The total amount of the one or more salts may be from about 10 wt. % to about 25 wt. %, about 30 wt. %, about 35 wt. %, about 40 wt. %, about 45 wt. %, or about 50 wt. %. The total amount of the one or more salts may be from about 15 wt. % to about 30 wt. %, about 35 wt. %, about 40 wt. %, about 45 wt. %, or about 50 wt. %. The total amount of the one or more salts may be from about 20 wt. % to about 40 wt. %, about 45 wt. %, or about 50 wt. %.

The total amount of the one or more salts of the hydroxy-polycarboxylic acid or the one or more alkaline earth metal salts, when used in a post-color treatment composition, is about 1 wt. % to about 75 wt. %, based on the total weight of the post-color treatment composition. The total amount of the one more salts may be from about 1 wt. % to about 25 wt. %, about 30 wt. %, about 35 wt. %, about 40 wt. %, about 45 wt. %, about 50 wt. %, about 55 wt. %, about 60 wt. %, about 65 wt. %, or about 70 wt. %. The total amount of the one more salts may be from about 5 wt. % to about 25 wt. %, about 30 wt. %, about 35 wt. %, about 40 wt. %, about 45 wt. %, about 50 wt. %, about 55 wt. %, about 60 wt. %, about 65 wt. %, or about 70 wt. %. The total amount of the one more salts may be from about 10 wt. % to about 25 wt. %, about 30 wt. %, about 35 wt. %, about 40 wt. %, about 45 wt. %, about 50 wt. %, about 55 wt. %, about 60 wt. %, about 65 wt. %, or about 70 wt. %. The total amount of the one more salts may be from about 15 wt. % to about 25 wt. %, about 30 wt. %, about 35 wt. %, about 40 wt. %, about 45 wt. %, about 50 wt. %, about 55 wt. %, about 60 wt. %, about 65 wt. %, or about 70 wt. %. The total amount of the one more salts may be from about 20 wt. % to about 40 wt. %, about 45 wt. %, about 50 wt. %, about 55 wt. %, about 60 wt. %, about 65 wt. %, or about 70 wt. %. The total amount of the one more salts may be from about 25 wt. % to about 40 wt. %, about 45 wt. %, about 50 wt. %, about 55 wt. %, about 60 wt. %, about 65 wt. %, or about 70 wt. %. The total amount of the one more salts may be from about 30 wt. % to about 45 wt. %, about 50 wt. %, about 55 wt. %, about 60 wt. %, about 65 wt. %, or about 70 wt. %.

The pre-color treatment compositions described herein are applied to the hair before applying the coloring composition. The pre-color treatment compositions are applied to the hair in a sufficient amount to cover the hair and are allowed to remain on the hair for a period of time. The pre-color treatment compositions are typically applied to the hair at room temperature (about 15° C. to about 25° C.) and allowed to at least briefly remain on the hair. For example, the pre-color treatment compositions may be allowed to remain on the hair for at least about 1, about 2, about 5, about 10, about 15, about 20, about 25, or about 30 minutes after application, or up to about 1 or about 2 hours, until the hair is subsequently colored. Further, the pre-treatment composition may be applied and allowed to remain on the hair for 1 to 30 minutes at room temperature (about 15° C. to about 25° C.). The post-color treatment compositions may be applied at higher temperatures, for example, at temperatures from about 20° C. to about 45° C., about 25° C. to about 45° C., about 30° C. to about 45° C. The compositions may be applied to the hair at one temperature, and then the hair containing the compositions may be warmed during treatment. Further, post-color treatment composition may be applied to the hair, and allowed to naturally dry on the hair, or a drying step may be included using heat and/or air (e.g., blow drying) to dry the composition onto the hair.

The pre-color treatment compositions may be applied to dry hair and allowed to remain on the hair for sufficient amount of time to absorb throughout the hair, and may optionally be dried onto the hair. For example, the hair may be blown dry after application of the pre-color treatment composition. The pre-color treatment composition may or may not be removed, e.g., by shampooing, prior to application of a coloring composition.

The coloring compositions described herein may be applied to the hair after application of a pre-color treatment composition in cases where a pre-color treatment composition is employed (as described above). The coloring compositions are typically applied to the hair within about 24 hours after treatment with the pre-color treatment composition, of within about 2 hours, about 1 hour, about 30 min, about 15 min, or about 5 min.

The coloring compositions are allowed to remain on the hair for a sufficient amount of time to adequately color the hair, as is well known in the art. For example, the coloring composition may be allowed to remain on the hair for 1 to 60 minutes at a temperature of 20 to 45° C. Typically, the coloring composition is allowed to remain on the hair for at least about 1 min., about 2 min., about 5 min., about 10 min., about 15 min., about 20 min., about 25 min., about 30 min. and may remain on the hair for up to about 1 hour, 1.5 hours, 2 hours, or longer. The amount of time that the coloring composition is allowed to remain on the hair often depends on the strength of the coloring composition, the original color and strength of the hair being colored, and the degree of color change desired. The coloring compositions may optionally be warmed upon application to the hair, for example, from a temperature of about 25° C., about 30° C., about 35° C., or higher, up to a temperature of about 40° C., or higher. The warming may expedite the coloring process.

Typically, after the coloring process is complete, the coloring composition is removed, for example, by shampooing, prior to application of a post-color treatment composition (in situations where a post-color treatment composition is applied). The colored hair may optionally be dried prior to application of a post-color treatment composition.

Typically, the post-color treatment composition is applied to the hair after the hair is colored, e.g., within 24 hours. Often, the post-color treatment composition is applied to the hair immediately after artificially coloring the hair, for example, within about 1 min., about 5 min., about 10 min., about 15 min., about 30 min., about 1 hour, or about 2 hours after artificially coloring the hair. The post-color treatment compositions described herein may be applied once, or may be applied multiple times. For example, the post-color treatment compositions may be applied daily, weekly, monthly, or applied during the time of washing the hair. The post-color treatment compositions may be "stand-alone" products or may be formulated as another cosmetic product that is applied to the hair, thereby creating a multi-purpose product. For example, the post-color treatment compositions may be formulated as a pre- or post-shampooing treatment or "rinse" product, it may be formulated as a conditioner, which is typically applied to the hair immediately after shampooing. It may be formulated as an "overnight" treatment to be applied to the hair and allowed to remain on the hair while the consumer sleeps.

The post-color treatment compositions may be applied to the hair at room temperature (about 15° C. to about 25° C.). Further, the post-color treatment compositions may be applied at higher temperatures, for example, at temperatures from about 20° C. to about 45° C., about 25° C. to about 45° C., about 30° C. to about 45° C. The compositions may be applied to the hair at one temperature, and then the hair containing the compositions may be warmed during treatment. Further, post-color treatment composition may be applied to the hair, and allowed to naturally dry on the hair, or a drying step may be included using heat and/or air (e.g., blow drying) to dry the composition onto the hair.

The coloring compositions of the present disclosure typically comprise at least one colorant compound chosen from oxidative dye precursors, direct dyes, pigments, and mixtures thereof. The oxidation dyes are generally chosen from one or more oxidation bases optionally combined with one or more couplers. The coloring composition may include an oxidation agent. In many cases an oxidative agent is combined with the coloring compositions immediately prior to treating hair with the coloring treatment.

Finally, the instant disclosure relates to kits comprising the compositions described herein, including the pre-color treatment compositions, the coloring compositions and the post-color treatment compositions. Each of the kits may also optionally include an oxidizing agent or a composition comprising an oxidizing agent. Often, the kits described herein are accompanied by instructions for use, and may also optionally include utensils for mixing, applying, and maintaining the compositions.

More exhaustive but non-limiting lists of components useful in the compositions disclosed herein are presented below.

Cosmetically Acceptable Solvent (or Carrier)

The compositions of the present disclosure may be presented in a cosmetically acceptable solvent. This cosmetically acceptable solvent may include, for example, water or a mixture of water and at least one cosmetically acceptable organic solvent.

As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol.

Other suitable examples of organic solvents are ethylene glycol, propylene glycol, butylene glycol, hexylene glycol, propane diol, and glycerin.

The organic solvents for use in the present disclosure can be volatile or non-volatile compounds.

The cosmetically acceptable solvent may be employed according to the present disclosure in an amount ranging from about 5% to about 95% by weight, or such as from about 20% to about 90% by weight, such as from about 30 to about 80% by weight, or such as from about 35% to about 75% by weight, such as from about 5 to about 50% by weight, such as from about 50 to 95% by weight, based on the total weight of the composition.

The organic solvent may be employed according to the present disclosure in an amount ranging from about 0.1% to about 25% by weight, such as from about 1% to about 15% by weight, or such as from about 3% to about 10% by weight, or such as from about 5% to about 10% by weight, based on the total weight of the disclosure composition of the present disclosure.

Colorants

The coloring compositions of the present disclosure include at least one colorant compound chosen from oxidative dye precursors, direct dyes, pigments, and mixtures thereof. The oxidation dyes are generally chosen from one or more oxidation bases optionally combined with one or more couplers. By way of example, the oxidation bases are chosen from para-phenylenediamines, bis(phenyl)alkylenediamines, para-aminophenols, ortho-aminophenols and heterocyclic bases, and the addition salts thereof.

Among the para-phenylenediamines that may be mentioned, for example, are para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(.beta.-hydroxyethyl)-para-phenylenediamine, 4-N,N-bis(.beta.-hydroxyethyl)amino-2-methylaniline, 4-N,N-bis(.beta.-hydroxyethyl)amino-2-chloroaniline, 2-.beta.-hydroxyethyl-para-phenylenediamine, 2-methoxymethyl-para-phenylenediamine, 2-fluoro-para-phenylenediamine, 2-isopropyl-para-phenylenediamine, N-(.beta.-hydroxypropyl)-para-phenylenediamine, 2-hydroxymethyl-para-phenylenediamine, N,N-dimethyl-3-methyl-para-phenylenediamine, N-ethyl-N-(beta.-hydroxyethyl)-para-phenylenediamine, N-(.beta.,.gamma.-dihydroxypropyl)-para-phenylenediamine, N-(4'-aminophenyl)-para-phenylenediamine, N-phenyl-para-phenylenediamine, 2-.beta.-hydroxyethyloxy-para-phenylenediamine, 2-.beta.-acetylaminoethyloxy-para-phenylenediamine, N-(beta.-methoxyethyl)-para-phenylenediamine, 4-aminophenylpyrrolidine, 2-thienyl-para-phenylenediamine, 2-.beta.- hydroxyethylamino-5-aminotoluene and 3-hydroxy-1-(4'-aminophenyl)pyrrolidine, and the addition salts thereof with an acid.

Among the para-phenylenediamines mentioned above, para-phenylenediamine, para-toluenediamine, 2-isopropyl-para-phenylenediamine, 2-.beta.-hydroxyethyl-para-phenylenediamine, 2-.beta.-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(beta.-hydroxyethyl)-para-phenylenediamine, 2-chloro-para-phenylenediamine and 2-.beta.-acetylaminoethyloxy-para-phenylenediamine, and the addition salts thereof with an acid, are particularly preferred.

Among the bis(phenyl)alkylenediamines that may be mentioned, for example, are N,N'-bis(beta.-hydroxyethyl)-N,N'-bis(4'-aminophenyl)-1,3-diaminopropano-I, N,N'-bis(beta.-hydroxyethyl)-N,N'-bis(4'-aminophenyl)ethylenediamine, N,N'-bis(4-aminophenyl)tetramethylenediamine, N,N'-bis(.beta.-hydroxyethyl)-N,N'-bis(4-aminophenyl)tetramethylenediamin-e, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(.beta.-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

Among the heterocyclic bases that may be mentioned, for example, are pyridine derivatives, pyrimidine derivatives and pyrazole derivatives.

Among the pyridine derivatives that may be mentioned are the compounds such as 2,5-diaminopyridine, 2-(4-methoxyphenyl)amino-3-aminopyridine and 3,4-diaminopyridine, and the addition salts thereof. Other pyridine oxidation bases that are useful in the present disclosure are the 3-aminopyrazolo[1,5-a]pyridine oxidation bases or the addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-Methanol, 2-(3-aminopyrazolo[1,5-a]pyrid-7-Methanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, 2-.quadrature.-hydroxyethoxy-3-amino-pyrazolo[1,5-a]pyridine; 2-(4-dimethylpyperazinium-1-yl)-3-amino-pyrazolo[1,5-a]pyridine; and the addition salts thereof.

More particularly oxidation bases that are useful in the present disclosure are selected from 3-aminopyrazolo-[1,5-a]-pyridines and preferably substituted on carbon atom 2 by:

(a) one (di)($C_1$-$C_6$)(alkyl)amino group wherein said alkyl group can be substituted by at least one hydroxy, amino, imidazolium group;

(b) one heterocycloalkyl group containing from 5 to 7 members chain, and from 1 to 3 heteroatoms, potentially cationic, potentially substituted by one or more ($C_1$-$C_6$-alkyl, such as di(C1-C4)alkylpiperazinium; or (c) one ($C_1$-$C_6$)alkoxy potentially substituted by one or more hydroxy groups such as .quadrature.-hydroxyalkoxy, and the addition salts thereof.

Among the pyrimidine derivatives that may be mentioned are compounds such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and their addition salts and their tautomeric forms, when a tautomeric equilibrium exists.

Among the pyrazole derivatives that may be mentioned are compounds such as 4,5-diamino-1-methyl-pyrazole, 4,5-diamino-1-(.beta.-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenyl-pyrazole, 4,5-diamino-1-methyl-3-phenylpyrazole, 4-amino-1,3-dimethyl-5-hydrazinopyrazole, 1-benzyl-4,5-diamino-3-methyl-pyrazole, 4,5-diamino-3-tert-butyl-1-methylpyrazole, 4,5-diamino-1-tert-butyl-3-methylpyrazole, 4,5-diamino-1-(.beta.-hydroxyethyl)-3-methylpyrazole, 4,5-diamino-1-ethyl-3-methyl-pyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(.beta.-hydroxyethyl)amino-1-methylpyrazole, and the addition salts thereof. 4,5-Diamino-1-(.beta.-methoxyethyl)pyrazole may also be used.

Pyrazole derivatives that may also be mentioned include diamino-N,N-dihydropyrazolopyrazolones such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-on-e, 4,5-diamino-1,2-dimethyl-1,2-dihydropyrazol-3-one, 4,5-diamino-1,2-diethyl-1,2-dihydropyrazol-3-one, 4,5-diamino-1,2-di-(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-o-ne. 2,3-Diamino-6,7-dihydro-1H,5H-pyrazolo[1,2-a]pyrazol-1-one and/or a salt thereof will preferably be used. 4,5-Diamino-1-(.beta.-hydroxyethyl)pyrazole and/or 2,3-diamino-6,7-dihydro-1H,5H-pyrazolo[1,2-a]pyrazol-1-one and/or a salt thereof will preferentially be used as heterocyclic bases.

Composition according to the present disclosure may optionally comprise one or more couplers advantageously chosen from those conventionally used in the dyeing or coloring of keratin fibers.

Among these couplers, mention may be made especially of meta-phenylenediamines, meta-aminophenols, meta-diphenols, naphthalene-based couplers and heterocyclic couplers, and also the addition salts thereof.

Mention may be made, for example, of 2-methyl-5-aminophenol, 5-N-(.beta.-hydroxyethyl)amino-2-methyl-phenol, 3-aminophenol, 5-amino-6-chloro-o-cresol (3-amino-2-chloro-6-methylphenol), 1,3-dihydroxybenzene, 1,3-dihydroxy-2-methyl-benzene, 4-chloro-1,3-dihydroxybenzene, 2,4-diamino-1-(.beta.-hydroxyethyloxy)benzene, 2-amino-4-(.beta.-hydroxyethylamino)-1-methoxybenzene, 1,3-diaminobenzene, 1,3-bis(2,4-diamino-phenoxy)propane, 3-ureidoaniline, 3-ureido-1-dimethylamino-benzene, sesamol, 1-.beta.-hydroxyethylamino-3,4-methylene-dioxybenzene, .alpha.-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(.beta.-hydroxyethyl)amino-3,4-methylene-dioxybenzene, 2,6-bis(J-hydroxyethylamino) toluene, 6-hydroxy-indoline, 2,6-dihydroxy-4-methylpyridine, 1-H-3-methylpyrazol-5-one, 1-phenyl-3-methylpyrazol-5-one, 2,6-dimethyl-pyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

In general, the addition salts of the oxidation bases and couplers that may be used in the context of the disclosure are especially selected from the addition salts with an acid such as the hydrochlorides, hydrobromides, sulfates, citrates, succinates, tartrates, lactates, tosylates, benzenesulfonates, phosphates and acetates.

The oxidation base(s) each advantageously represent from 0.001% to 10% by weight relative to the total weight of the composition, and preferably from 0.005% to 5% by weight relative to the total weight of the compositions of the present disclosure.

The coupler(s), if they are present, each advantageously represent from 0.001% to 10% by weight relative to the total weight of the composition, and preferably from 0.005% to 5% by weight relative to the total weight of the compositions of the present disclosure.

Compositions according to the disclosure may optionally comprise b) one or more synthetic or natural direct dyes, chosen from anionic and nonionic species, preferably cationic or nonionic species, either as sole dyes or in addition to the oxidation dye(s).

Examples of suitable direct dyes that may be mentioned include azo direct dyes; (poly)methine dyes such as cyanins, hemicyanins and styryls; carbonyl dyes; azine dyes; nitro (hetero)aryl dyes; tri(hetero)arylmethane dyes; porphyrin dyes; phthalocyanin dyes, and natural direct dyes, alone or as mixtures.

Many direct dyes are cationic direct dyes. Mention may be made of the hydrazono cationic dyes of formulas (Va) and (V'a), the azo cationic dyes (VIa) and (VI'a) and the diazo cationic dyes (VIIa) below:

$$Het^+ - C(R^a) = N - N(R^b) - Ar, An^-  \quad (Va)$$

$$Het^+ - N(R^a) - N = C(R^b) - Ar, An^-  \quad (V'a)$$

$$Het^+ - N = N - Ar, An^-  \quad (VIa)$$

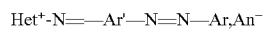

in which formulas (Va), (V'a), (VIa), (VI'a) and (VIIa):

Het⁺ represents a cationic heteroaryl radical, preferably bearing an endocyclic cationic charge, such as imidazolium, indolium or pyridinium, optionally substituted preferentially with one or more ($C_1$-$C_8$) alkyl groups such as methyl;

Ar⁺ representing an aryl radical, such as phenyl or naphthyl, bearing an exocyclic cationic charge, preferentially ammonium, particularly tri($C_1$-$C_8$)alkylammonium such as trimethylammonium;

Ar represents an aryl group, especially phenyl, which is optionally substituted, preferentially with one or more electron-donating groups such as i) optionally substituted ($C_1$-$C_8$)alkyl, ii) optionally substituted ($C_1$-$C_8$) alkoxy, iii) (di)($C_1$-$C_8$)(alkyl)amino optionally substituted on the alkyl group(s) with a hydroxyl group, iv) aryl($C_1$-$C_8$)alkylamino, v) optionally substituted N—($C_1$-$C_8$)alkyl-N-aryl($C_1$-$C_8$)alkylamino or alternatively Ar represents a julolidine group;

Ar' is an optionally substituted divalent (hetero)arylene group such as phenylene, particularly para-phenylene, or naphthalene, which are optionally substituted, preferentially with one or more groups ($C_1$-$C_8$)alkyl, hydroxyl or ($C_1$-$C_8$)alkoxy Ar" is an optionally substituted (hetero)aryl group such as phenyl or pyrazolyl, which are optionally substituted, preferentially with one or more groups ($C_1$-$C_8$)alkyl, hydroxyl, (di)($C_1$-$C_8$)(alkyl)amino, ($C_1$-$C_8$)alkoxy or phenyl;

$R^a$ and $R^b$, which may be identical or different, represent a hydrogen atom or a group ($C_1$-$C_8$)alkyl, which is optionally substituted, preferentially with a hydroxyl group;

or alternatively the substituent $R^a$ with a substituent of Het⁺ and/or $R_b$ with a substituent of Ar and/or $R^a$ with $R_b$ form, together with the atoms that bear them, a (hetero)cycloalkyl;

particularly, $R^a$ and $R_b$ represent a hydrogen atom or a group ($C_1$-$C_4$)alkyl, which is optionally substituted with a hydroxyl group;

An⁻ represents an anionic counter-ion such as mesylate or halide. In particular, mention may be made of the azo and hydrazono cationic dyes bearing an endocyclic cationic charge of formulae (Va), (V'a) and (VIa) as defined previously. More particularly those of formulae (Va), (V'a) and (VIa) derived from the dyes described in patent applications WO 95/15144, WO 95/01772 and EP-714954, which are incorporated herein by reference in their entirety.

In some cases, the cationic part is derived from the following derivatives:

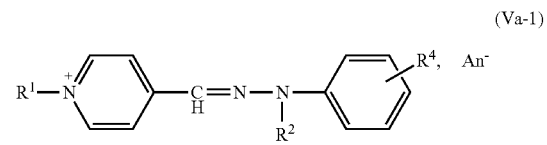

(Va-1)

-continued

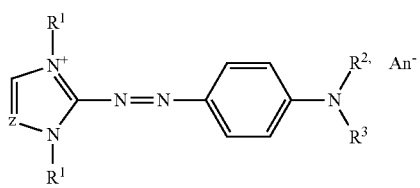
(VIa-1)

formulae (V-1) and (VI-1) with:

$R^1$ representing a ($C_1$-$C_4$) alkyl group such as methyl;

$R^2$ and $R^3$, which are identical or different, represent a hydrogen atom or a ($C_1$-$C_4$)alkyl group, such as methyl; and $R^4$ represents a hydrogen atom or an electron-donating group such as optionally substituted ($C_1$-$C_8$)alkyl, optionally substituted ($C_1$-$C_8$)alkoxy, or (di)($C_1$-$C_8$)(alkyl)amino optionally substituted on the alkyl group(s) with a hydroxyl group; particularly, $R^4$ is a hydrogen atom, Z represents a CH group or a nitrogen atom, preferentially CH;

An⁻ represents an anionic counter-ion such as mesylate or halide.

Particularly, the dye of formulae (Va-1) and (VIa-1) is chosen from Basic Red 51, Basic Yellow 87 and Basic Orange 31 or derivatives thereof:

Basic Red 51

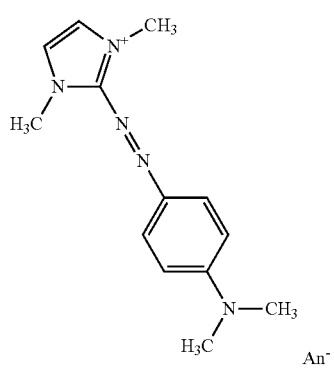

Basic Orange 31

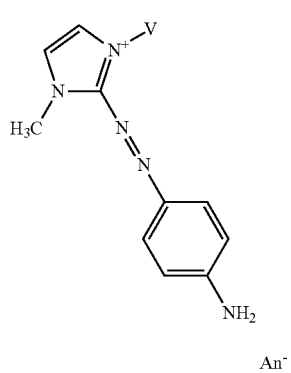

Basic Yellow 87

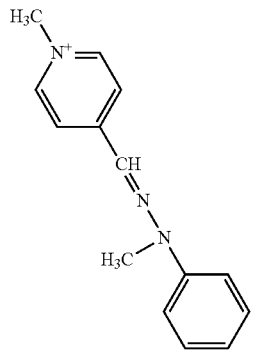

Among the natural direct dyes that may be used according to the disclosure, mention may be made of lawsone, juglone, alizarin, purpurin, carminic acid, kermesic acid, purpurogallin, protocatechaldehyde, indigo, isatin, curcumin, spinulosin, apigenidin and orceins. Extracts or decoctions containing these natural dyes and in particular henna-based poultices or extracts may also be used.

When they are present, the direct dye(s) more particularly represent from 0.001% to 10% by weight and preferably from 0.005% to 5% by weight of the total weight of the compositions of the present disclosure.

Surfactants

The various compositions described herein may include one or more surfactants, including cationic, anionic, non-ionic and/or amphoteric/zwitterionic surfactants. Non-limiting examples of surfactants that may be used are provided below.

Cationic Surfactants

The term "cationic surfactant" means a surfactant that is positively charged when it is contained in the composition according to the disclosure. This surfactant may bear one or more positive permanent charges or may contain one or more functions that are cationizable in the composition according to the disclosure.

Non-limiting examples of cationic surfactants include behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride(Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, and hexadecyltrimethyl ammonium bromide.

The cationic surfactant(s) may be chosen from optionally polyoxyalkylenated, primary, secondary or tertiary fatty amines, or salts thereof, and quaternary ammonium salts, and mixtures thereof.

The fatty amines generally comprise at least one $C_8$-$C_{30}$ hydrocarbon-based chain.

Examples of quaternary ammonium salts that may especially be mentioned include: those corresponding to the general formula (III) below:

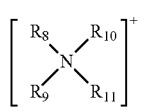

(III)

in which the groups $R_8$ to $R_{11}$, which may be identical or different, represent a linear or branched, saturated or unsaturated aliphatic group comprising from 1 to 30 carbon atoms, or an aromatic group such as aryl or alkylaryl, at least one of the groups $R_8$ to $R_{11}$ denoting a group comprising from 8 to 30 carbon atoms and preferably from 12 to 24 carbon atoms. The aliphatic groups may comprise heteroatoms especially such as oxygen, nitrogen, sulfur and halogens. The aliphatic groups are chosen, for example, from $C_1$-$C_{30}$ alkyl, $C_2$-$C_{30}$ alkenyl, $C_1$-$C_{30}$ alkoxy, polyoxy($C_2$-$C_6$)alkylene, $C_1$-$C_{30}$ alkylamide, ($C_{12}$-$C_{22}$)alkylamido($C_2$-$C_6$)alkyl, ($C_{12}$-$C_{22}$)alkyl acetate and $C_1$-$C_{30}$ hydroxyalkyl groups; $X^-$ is an anion chosen from the group of halides, phosphates, acetates, lactates, ($C_1$-$C_4$)alkyl sulfates, and ($C_1$-$C_4$)alkyl- or ($C_1$-$C_4$)alkylarylsulfonates.

Among the quaternary ammonium salts of formula (III), those that are preferred are, on the one hand, tetraalkylammonium salts, for instance dialkyldimethylammonium or alkyltrimethylammonium salts in which the alkyl group contains approximately from 12 to 22 carbon atoms, in particular behenyltrimethylammonium, distearyldimethylammonium, cetyltrimethylammonium or benzyldimethylstearylammonium salts, or, on the other hand, oleocetyldimethylhydroxyethylammonium salts, palmitylamidopropyltrimethylammonium salts, stearamidopropyltrimethylammonium salts and stearamidopropyldimethylcetearylammonium salts.

In some cases it is useful to use salts such as the chloride salts of the following compounds:

A. a quaternary ammonium salt of imidazoline, such as, for example, those of formula (IV) below:

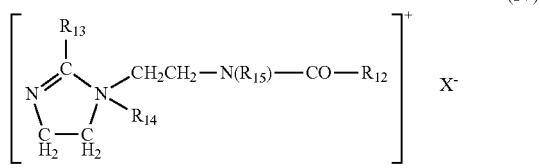

(IV)

in which $R_{12}$ represents an alkenyl or alkyl group comprising from 8 to 30 carbon atoms, derived for example from tallow fatty acids, $R_{13}$ represents a hydrogen atom, a $C_1$-$C_4$ alkyl group or an alkyl or alkenyl group comprising from 8 to 30 carbon atoms, $R_{14}$ represents a $C_1$-$C_4$ alkyl group, $R_{15}$ represents a hydrogen atom or a $C_1$-$C_4$ alkyl group, $X^-$ is an anion chosen from the group of halides, phosphates, acetates, lactates, alkyl sulfates, alkyl- or alkylaryl-sulfonates in which the alkyl and aryl groups preferably comprise, respectively, from 1 to 20 carbon atoms and from 6 to 30 carbon atoms. $R_{12}$ and $R_{13}$ preferably denote a mixture of alkenyl or alkyl groups containing from 12 to 21 carbon atoms, derived for example from tallow fatty acids, $R_{14}$ preferably denotes a methyl group, and $R_{15}$ preferably denotes a hydrogen atom. Such a product is sold, for example, under the name Rewoquat® W 75 by the company Rewo;

B. a quaternary diammonium or triammonium salt, in particular of formula (V):

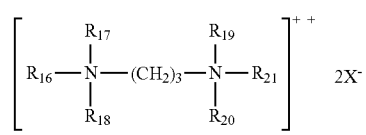

(V)

in which $R_{16}$ denotes an alkyl radical comprising approximately from 16 to 30 carbon atoms, which is optionally hydroxylated and/or interrupted with one or more oxygen atoms, $R_{17}$ is chosen from hydrogen or an alkyl radical comprising from 1 to 4 carbon atoms or a group ($R_{16a}$)($R_{17a}$)($R_{18a}$)N—(CH$_2$)$_3$, $R_{16a}$, $R_{17a}$, $R_{18a}$, $R_{15}$, $R_{19}$, $R_{20}$ and $R_{21}$, which may be identical or different, being chosen from hydrogen and an alkyl radical comprising from 1 to 4 carbon atoms, and $X^-$ is an anion chosen from the group of halides, acetates, phosphates, nitrates and methyl sulfates. Such compounds are, for example, Finquat CT-P, sold by the company Finetex (Quaternium 89), and Finquat CT, sold by the company Finetex (Quaternium 75), C. a quaternary ammonium salt containing at least one ester function, such as those of formula (VI) below:

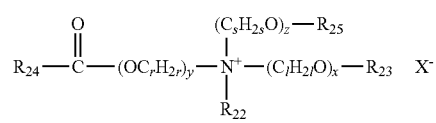

(VI)

in which:

$R_{22}$ is chosen from $C_1$-$C_6$ alkyl groups and $C_1$-$C_6$ hydroxyalkyl or dihydroxyalkyl groups;

$R_{23}$ is chosen from:

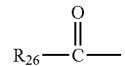

$R_{27}$, which is a linear or branched, saturated or unsaturated $C_1$-$C_{22}$ hydrocarbon-based group, and a hydrogen atom, $R_{25}$ is chosen from:

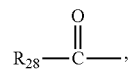

$R_{29}$, which is a linear or branched, saturated or unsaturated $C_1$-$C_6$ hydrocarbon-based group, and a hydrogen atom, $R_{24}$, $R_{26}$ and $R_{25}$, which may be identical or different, are chosen from linear or branched, saturated or unsaturated $C_7$-$C_{21}$ hydrocarbon-based groups;

r, s and t, which may be identical or different, are integers ranging from 2 to 6;

y is an integer ranging from 1 to 10;

x and z, which may be identical or different, are integers ranging from 0 to 10;

$X^-$ is a simple or complex, organic or mineral anion;

with the proviso that the sum x+y+z is from 1 to 15, that when x is 0 then $R_n$ denotes $R_{27}$, and that when z is 0 then $R_{25}$ denotes $R_{29}$.

The alkyl groups $R_{22}$ may be linear or branched, and more particularly linear. In some cases, $R_{22}$ denotes a methyl, ethyl, hydroxyethyl or dihydroxypropyl group, and more particularly a methyl or ethyl group. Advantageously, the sum x+y+z is from 1 to 10.

When $R_{23}$ is a hydrocarbon-based group $R_{27}$, it may be long and contain from 12 to 22 carbon atoms, or may be short and contain from 1 to 3 carbon atoms. When $R_{25}$ is an $R_{29}$ hydrocarbon-based group, it preferably contains 1 to 3 carbon atoms. Advantageously, $R_{24}$, $R_{26}$ and $R_{28}$, which may be identical or different, are chosen from linear or branched, saturated or unsaturated $C_{11}$-$C_{21}$ hydrocarbon-based groups, and more particularly from linear or branched, saturated or unsaturated $C_{11}$-$C_{21}$ alkyl and alkenyl groups.

In some cases, x and z, which may be identical or different, have values of 0 or 1. Likewise, in some cases y is equal to 1. In some cases, r, s and t, which may be identical or different, are equal to 2 or 3, and even more particularly are equal to 2.

The anion $X^-$ is may be a halide (chloride, bromide or iodide) or an alkyl sulfate, more particularly methyl sulfate. However, use may be made of methanesulfonate, phosphate, nitrate, tosylate, an anion derived from an organic acid, such as acetate or lactate, or any other anion compatible with the ammonium containing an ester function.

The anion $X^-$ is even more particularly chloride or methyl sulfate.

Use is made more particularly, in the composition according to the invention, of the ammonium salts of formula (VI) in which:

$R_{22}$ denotes a methyl or ethyl group, x and y are equal to 1;

z is equal to 0 or 1;

r, s and t are equal to 2;

$R_{23}$ is chosen from:

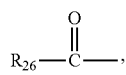

methyl, ethyl or $C_{14}$-$C_{22}$ hydrocarbon-based groups, and a hydrogen atom;

$R_{25}$ is chosen from:

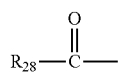

and a hydrogen atom;

$R_{24}$, $R_{26}$ and $R_{28}$, which may be identical or different, are chosen from linear or branched, saturated or unsaturated $C_{13}$-$C_{17}$ hydrocarbon-based groups, and preferably from linear or branched, saturated or unsaturated $C_{13}$-$C_{17}$ alkyl and alkenyl groups. The hydrocarbon-based groups are advantageously linear.

Mention may be made, for example, of the compounds of formula (VI) such as the diacyloxyethyldimethylammonium, diacylo xyethylhydroxyethylmethylammonium, monoacyloxyethyldihydroxyethylmethylammonium, triacyloxyethylmethylammonium and monoacyloxyethylhydroxyethyldimethylammonium salts (chloride or methyl sulfate in particular), and mixtures thereof. The acyl groups preferably contain 14 to 18 carbon atoms and are obtained more particularly from a plant oil, such as palm oil or sunflower oil. When the compound contains several acyl groups, these groups may be identical or different.

These products are obtained, for example, by direct esterification of triethanolamine, triisopropanolamine, an alkyldiethanolamine or an alkyldiisopropanolamine, which are optionally oxyalkylenated, with $C_{10}$-$C_{30}$ fatty acids or with mixtures of $C_{10}$-$C_{30}$ fatty acids of plant or animal origin, or by transesterification of the methyl esters thereof. This esterification is followed by quaternization using an alkylating agent such as an alkyl (preferably methyl or ethyl) halide, a dialkyl (preferably methyl or ethyl) sulfate, methyl methanesulfonate, methyl para-toluenesulfonate, glycol chlorohydrin or glycerol chlorohydrin. Such compounds are, for example, sold under the names Dehyquart® by the company Henkel, Stepanquat® by the company Stepan, Noxamium® by the company Ceca or Rewoquat® WE 18 by the company Rewo-Witco.

The composition according to the invention may contain, for example, a mixture of quaternary ammonium monoester, diester and triester salts with a weight majority of diester salts.

Use may be made of behenoylhydroxypropyltrimethylammonium chloride, provided by Kao under the name Quatarmin BTC 131.

Nonionic Surfactants

Examples of nonionic surfactants that may be used are described, for example, in the Handbook of Surfactants by M. R. Porter, published by Blackie & Son (Glasgow and London), 1991, pp. 116-178, which is incorporated herein by reference in its entirety. The nonionic surfactant may be alcohols, alpha-diols and ($C_1$-$C_{24}$)alkylphenols, these compounds being polyethoxylated, polypropoxylated and/or polyglycerolated, and containing at least one fatty chain comprising, for example, from 8 to 18 carbon atoms, it being possible for the number of ethylene oxide and/or propylene oxide groups to especially range from 2 to 50, and for the number of glycerol groups to especially range from 2 to 30.

Mention may also be made of copolymers of ethylene oxide and propylene oxide, optionally oxyethylenated sorbitan fatty acid esters, sucrose fatty acid esters, polyoxyalkylenated fatty acid esters, polyoxyalkylenated fatty amides, optionally oxyalkylenated alkyl(poly)glucosides, alkylglucoside esters, derivatives of N-alkylglucamine and of N-acylmethylglucamine, aldobionamides, amine oxides and (poly)oxyalkylenated silicones.

The nonionic surfactants are more particularly chosen from monooxyalkylenated or polyoxyalkylenated and monoglycerolated or polyglycerolated nonionic surfactants, and alkyl(poly)glucosides. The oxyalkylene units are more particularly oxyethylene or oxypropylene units, or a combination thereof, preferably oxyethylene units.

Useful nonionic surfactants may include: oxyalkylenated ($C_8$-$C_{24}$)alkylphenols; saturated or unsaturated, linear or branched, oxyalkylenated $C_8$-$C_{40}$ alcohols; saturated or unsaturated, linear or branched, oxyalkylenated $C_8$-$C_{30}$ amides; esters of saturated or unsaturated, linear or branched, $C_8$-$C_{30}$ acids and of polyethylene glycols; saturated or unsaturated, oxyethylenated plant oils; condensates of ethylene oxide and/or of propylene oxide, alone or as mixtures; oxyethylenated and/or oxypropylenated silicones; and alkyl(poly)glucosides.

As examples of monoglycerolated or polyglycerolated nonionic surfactants, monoglycerolated or polyglycerolated $C_8$-$C_{40}$ alcohols are useable. In particular, the monoglycerolated or polyglycerolated C $C_8$-$C_{40}$ alcohols correspond to formula (VIII) below:

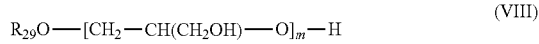
(VIII)

in which formula (VIII):

$R_{29}$ represents a linear or branched $C_8$-$C_{40}$ and preferably $C_8$-$C_{30}$ alkyl or alkenyl radical; and m represents a number ranging from 1 to 30, or from 1 to 10.

As examples of compounds of formula (VIII), mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol of formula (VIII) may represent a mixture of alcohols in the same way that the value of m represents a statistical value, which means that, in a commercial product, several species of polyglycerolated fatty alcohols may coexist in the form of a mixture.

The alkyl(poly)glycoside nonionic surfactant(s) may be represented by formula (IX) below:

(IX)

in which:

$R_{30}$ represents a saturated or unsaturated, linear or branched alkyl group comprising from about 8 to 24 carbon atoms, or an alkylphenyl group in which the linear or branched alkyl group comprises from 8 to 24 carbon atoms;

$R_{31}$ represents an alkylene group containing from about 2 to 4 carbon atoms, G represents a saccharide unit comprising from 5 to 6 carbon atoms, t denotes a value ranging from 0 to 10, or from 0 to 4, and v denotes a value ranging from 1 to 15.

In some cases, the alkyl(poly)glycoside nonionic surfactant(s) correspond to formula (IX) in which:

$R_{30}$ denotes a linear or branched, saturated or unsaturated alkyl group containing from 8 to 18 carbon atoms, G denotes glucose, fructose or galactose, preferably glucose, t denotes a value ranging from 0 to 3, and is preferably equal to 0, and $R_{31}$ and v are as defined previously.

The degree of polymerization of the alkyl(poly)glucoside nonionic surfactant(s), as represented, for example, by the index v in formula (IX), ranges on average from 1 to 15, or from 1 to 4. This degree of polymerization more particularly ranges from 1 to 2 and better still from 1.1 to 1.5, on average.

The glycoside bonds between the saccharide units are of 1.6 or 1.4 type and preferably of 1.4 type.

Examples of compounds of formula (IX) that may especially be mentioned are the products sold by the company Cognis under the names Plantaren® (600 CS/U, 1200 and 2000) or Plantacare® (818, 1200 and 2000). Use may also be made of the products sold by the company SEPPIC under the names Triton CG 110 (or Oramix CG 110) and Triton CG 312 (or Oramix® NS 10), the products sold by the company BASF under the name Lutensol GD 70 or the products sold by the company Chem Y under the name AG10 LK. Use may also be made, for example, of the 1,4-($C_8$-$C_{18}$)alkyl-polyglucoside as an aqueous solution at 53% by weight relative to the total weight of the solution, sold by Cognis under the reference Plantacare® 818 UP.

Amphoteric or Zwitterionic Surfactants

The amphoteric or zwitterionic surfactant that may be used in compositions according to the disclosure may be derivatives of aliphatic secondary or tertiary amines, optionally quaternized, in which derivatives the aliphatic group is a linear or branched chain comprising from 8 to 22 carbon atoms, the amine derivatives containing at least one anionic group, such as a carboxylate, sulfonate, sulfate, phosphate or phosphonate group. Mention may be made in particular of ($C_8$-$C_{20}$)alkylbetaines such as cocoylbetaine, sulfobetaines, ($C_8$-$C_{20}$)alkylamido($C_2$-$C_8$)alkylbetaines such as cocoylamidopropylbetaine or ($C_8$-$C_{20}$)alkylamido($C_8$-$C_8$)-alkyl-sulfobetaines, and mixtures thereof.

Among the derivatives of aliphatic secondary or tertiary amines, optionally quaternized, that may be used, as defined above, mention may also be made of the compounds of respective structures (I), (II) and (IIa) below:

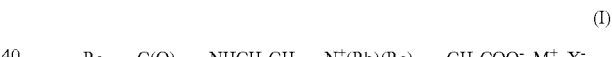
(I)

in which formula (I):

Ra represents a $C_{10}$-$C_{30}$ alkyl or alkenyl group derived from an acid Ra-COOH preferably present in hydrolysed coconut oil, or a heptyl, nonyl or undecyl group; Rb represents a beta-hydroxyethyl group; and Rc represents a carboxymethyl group;

$M^+$ represents a cationic counterion derived from an alkali metal or alkaline-earth metal, such as sodium, an ammonium ion or an ion derived from an organic amine; and $X^-$ represents an organic or mineral anionic counterion, such as that chosen from halides, acetates, phosphates, nitrates, ($C_1$-$C_4$)alkyl sulfates, ($C_1$-$C_4$)alkyl- or ($C_1$-$C_4$) alkylarylsulfonates, in particular methyl sulfate and ethyl sulfate; or alternatively $M^+$ and $X^-$ are absent;

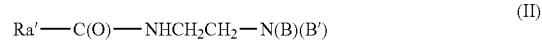
(II)

in which formula (II):

B represents the group —$CH_2$—$CH_2$—O—X'; B' represents the group —$(CH_2)_z$Y', with z=1 or 2;

X' represents the group —$CH_2$—COOH, $CH_2$—COOZ', —$CH_2CH_2$—COOH or —$CH_2CH_2$—COOZ', or a hydrogen atom;

Y' represents the group —COOH, —COOZ', CH$_2$CH(OH)SO$_3$H or the group —CH$_2$CH(OH)SO$_3$Z';

Z' represents a cationic counterion derived from an alkali metal or alkaline-earth metal, such as sodium, an ammonium ion or an ion derived from an organic amine;

Ra' represents a C$_{10}$-C$_{30}$ alkyl or alkenyl group of an acid Ra'-COOH, which may be coconut oil or in hydrolysed linseed oil, or an alkyl group, especially a C$_{17}$ group and its iso form, or an unsaturated C$_{17}$ group.

The compounds of this type are classified in the CTFA dictionary, 5th edition, 1993, under the names disodium cocoamphodiacetate, disodium lauroamphodiacetate, disodium caprylamphodiacetate, disodium caprylamphodiacetate, disodium cocoamphodipropionate, disodium lauroamphodipropionate, disodium caprylamphodipropionate, disodium caprylamphodipropionate, lauroamphodipropionic acid and cocoamphodipropionic acid.

By way of example, mention may be made of the cocoamphodiacetate sold by the company Rhodia under the trade name Miranol C2M Concentrate and the cocoamphodipropionate sold by the company Evonik Goldschmidt under the trade name Rewoteric AM KSF 40.

$$Ra''-NH-CH(Y'')-(CH_2)_n-C(O)-NH-(CH_2)_{n'}-N(Rd)(Re) \quad (IIa)$$

in which formula (IIa):

Y" represents the group —COOH, —COOZ", —CH$_2$CH(OH)SO$_3$H or the group —CH$_2$CH(OH)SO$_3$Z";

Rd and Re, independently of each other, represent a C$_1$-C$_4$ alkyl or hydroxyalkyl radical;

Z" represents a cationic counterion derived from an alkali metal or alkaline-earth metal, such as sodium, an ammonium ion or an ion derived from an organic amine;

Ra" represents a C$_{10}$-C$_{30}$ alkyl or alkenyl group of an acid Ra"-COOH;

n and n' denote, independently of each other, an integer ranging from 1 to 3; and mixtures of these compounds.

Among the compounds of formula (IIa), mention may be made of the compound classified in the CTFA dictionary under the name sodium diethylaminopropyl cocoaspartamide and sold by the company Chimex under the name Chimexane HB. In some instances, the amphoteric or zwitterionic surfactant(s) are chosen from cocoylbetaine, cocoylamidopropylbetaine and sodium cocoylamidoethyl-N-hydroxyethylaminopropionate.

The term "anionic surfactant" means a surfactant comprising, as ionic or ionizable groups, only anionic groups. These anionic groups are chosen preferably from the groups CO$_2$H, CO$_2^-$, SO$_3$H, SO$_3^-$, OSO$_3$H, OSO$_3^-$ O$_2$PO$_2$H, O$_2$PO$_2$H and O$_2$PO$_2^{2-}$.

The anionic surfactant(s) that may be used may be alkyl sulfates, alkyl ether sulfates, alkylamido ether sulfates, alkylaryl polyether sulfates, monoglyceride sulfates, alkylsulfonates, alkylamide sulfonates, alkylarylsulfonates, alpha-olefin sulfonates, paraffin sulfonates, alkylsulfosuccinates, alkyl ether sulfosuccinates, alkylamide sulfosuccinates, alkyl sulfoacetates, acylsarcosinates, acylglutamates, alkylsulfosuccinamates, acylisethionates and N-acyltaurates, salts of alkyl monoesters and polyglycoside-polycarboxylic acids, acyllactylates, salts of D-galactoside uronic acids, salts of alkyl ether carboxylic acids, salts of alkyl aryl ether carboxylic acids, and salts of alkylamido ether carboxylic acids; or the non-salified forms of all of these compounds, the alkyl and acyl groups of all of these compounds containing from 6 to 24 carbon atoms and the aryl group denoting a phenyl group. Some of these compounds may be oxyethylenated and then preferably comprise from 1 to 50 ethylene oxide units.

The salts of C$_6$-C$_{24}$ alkyl monoesters of polyglycoside-polycarboxylic acids may be chosen from C$_6$-C$_{24}$ alkyl polyglycoside-citrates, C$_6$-C$_{24}$ alkyl polyglycoside-tartrates and C$_6$-C$_{24}$ alkyl polyglycoside-sulfo succinates.

When the anionic surfactant(s) are in salt form, they may be chosen especially from alkali metal salts such as the sodium or potassium salt and preferably the sodium salt, ammonium salts, amine salts and in particular amino alcohol salts, or alkaline-earth metal salts such as the magnesium salt.

Examples of amino alcohol salts that may especially be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts. Alkali metal or alkaline-earth metal salts and in particular the sodium or magnesium salts may be used.

Use is also made of (C$_6$-C$_{24}$)alkyl sulfates, (C$_6$-C$_{24}$)alkyl ether sulfates, which are optionally ethoxylated, comprising from 2 to 50 ethylene oxide units, and mixtures thereof, in particular in the form of alkali metal salts or alkaline-earth metal salts, ammonium salts or amino alcohol salts. More preferentially, the anionic surfactant(s) are chosen from (C$_{10}$-C$_{20}$)alkyl ether sulfates, and in particular sodium lauryl ether sulfate containing 2.2 mol of ethylene oxide.

Oxidizing Agent

Oxidizing agents may be selected from, for example, peroxides, persulfates, perborates percarbonates, alkali metal bromates, ferricyanides, peroxygenated salts, or a mixture thereof. Oxidizing agents that may also be used include at least one redox enzyme such as laccases, peroxidases, and 2-electron oxidoreductases, such as uricase, where appropriate in the presence of their respective donor or co-factor. Oxygen in the air may also be employed as an oxidizing agent.

In some cases, the oxidizing agent is hydrogen peroxide present in an aqueous solution whose titre may range from 1 to 40 volumes, such as from 5 to 40 volumes or such as from 5 to 20 volumes.

In other cases, the oxidizing agent is a persulfate and/or a monopersulfate such as, for example, potassium persulfate, sodium persulfate, ammonium persulfate, as well as mixtures thereof. In one embodiment, the oxidizing agents in the present disclosure are selected from hydrogen peroxide, potassium persulfate, sodium persulfate, and mixtures thereof. Hydrogen peroxide may commonly be used as the oxidizing agent.

In general, the oxidizing agent will be present in an amount of from about 0.05 to about 50% by weight, such as from about 0.1% to about 30% by weight, or such as from about 0.1% to about 20% by weight, or such as from about 1% to about 10% by weight, based on the total weight of the oxidizing composition.

In some instances, the oxidizing composition is aqueous or is in the form of an emulsion.

In other instances, the oxidizing composition is substantially anhydrous. The term "substantially anhydrous" means that the oxidizing composition is either completely free of water or contains no appreciable amount of water, for example, no more than 5% by weight, or no more than 2% by weight, or no more than 1% by weight, based on the weight of the oxidizing composition. It should be noted that this refers for example to bound water, such as the water of crystallization of the salts or traces of water absorbed by the raw materials used in the preparation of the compositions according to the disclosure.

The oxidizing composition can contain at least one solvent, chosen from water, organic solvents, and mixtures thereof. When the oxidizing composition is substantially anhydrous, the oxidizing composition may comprise at least one solvent chosen from organic solvents. Suitable organic solvents for use in the oxidizing composition include ethanol, isopropyl alcohol, propanol, benzyl alcohol, phenyl ethyl alcohol, glycols and glycol ethers, such as propylene glycol, hexylene glycol, ethylene glycol monomethyl, monoethyl or monobutyl ether, propylene glycol and its ethers, such as propylene glycol monomethyl ether, butylene glycol, dipropylene glycol, diethylene glycol alkyl ethers, such as diethylene glycol monoethyl ether and monobutyl ether, ethylene glycol, propylene glycol, butylene glycol, hexylene glycol, propane diol, glycerin, hydrocarbons such as straight chain hydrocarbons, mineral oil, polybutene, hydrogenated polyisobutene, hydrogenated polydecene, polydecene, squalane, petrolatum, isoparaffins, and mixtures, thereof.

The organic solvent may, for example, be present in an amount ranging from about 0.5% to about 70% by weight, such as from about 2% to about 60% by weight, preferably from about 5 to about 50% by weight, relative to the total weight of the oxidizing composition.

The oxidizing composition may be in the form of a powder, gel, liquid, foam, lotion, cream, mousse, and emulsion.

The oxidizing composition of the present disclosure my also contain at least one fatty substance as described above. Thus, the total amount of fatty substances in the combination or mixture of the cosmetic and oxidizing compositions of the present disclosure may range from about 10% to about 80% by weight, or such as from about 20% to about 60% by weight, or such as from about 20% to about 40% by weight, or such as from about 20% to about 30% by weight, based on the total weight of the composition.

Preservatives

One or more preservatives may be included in the compositions described herein for treating hair. Suitable preservatives include, but are not limited to, glycerin containing compounds (e.g., glycerin or ethylhexylglycerin or phenoxyethanol), benzyl alcohol, parabens (methylparaben, ethylparaben, propylparaben, butylparaben, isobutylparaben, etc.), sodium benzoate, ethylenediamine-tetraacetic acid (EDTA), potassium sorbate, and/or grapefruit seed extract, or combinations thereof. More than one preservative may be included in the composition. Other preservatives are known in the cosmetics industries and include salicylic acid, DMDM Hydantoin, Formaldahyde, Chlorphenism, Triclosan, Imidazolidinyl Urea, Diazolidinyl Urea, Sorbic Acid, Methylisothiazolinone, Sodium Dehydroacetate, Dehydroacetic Acid, Quaternium-15, Stearalkonium Chloride, Zinc Pyrithione, Sodium Metabisulfite, 2-Bromo-2-Nitropropane, Chlorhexidine Digluconate, Polyaminopropyl biguanide, Benzalkonium Chloride, Sodium Sulfite, Sodium Salicylate, Citric Acid, Neem Oil, Essential Oils (various), Lactic Acid, and Vitamin E (tocopherol).

The preservative is optionally included in an amount ranging from about 0.01 wt. % to about 5 wt. %, about 0.15% to about 1 wt. %, or about 1 wt. % to about 3 wt. %, based on the total weight of the composition.

Viscosity Modifying Agents

The compositions may contain one or more viscosity modifying agents, such as viscosity increasing agents. Classes of such agents include, but are not limited to, viscous liquids, such as polyethylene glycol, semisynthetic polymers, such as semisynthetic cellulose derivatives, synthetic polymers, such as carbomers, poloxamers, and polyethyleneimines (e.g., PEI-10), naturally occurring polymers, such as acacia, tragacanth, alginates (e.g., sodium alginate), carrageenan, vegetable gums, such as xanthan gum, petroleum jelly, waxes, particulate associate colloids, such as bentonite, colloidal silicon dioxide, and microcrystalline cellulose, surfactants, such as PPG-2 hydroxyethyl coco/isostearamide, emulsifiers, such as disteareth-75 IPDI, and salts, such as sodium chloride, and combinations thereof.

Forms

The compositions described herein may be in any suitable physical form. Suitable forms include, but are not limited to low to moderate viscosity liquids, lotions, milks, mousses, sprays, gels, creams, conditioners, and the like. Suitable excipients, such as those listed above, are included or excluded from the hair care formulation depending on the form of use of the formulation (e.g., hair spray, cream, conditioner, etc.).

i. Spray

The compositions described herein for treating hair may be in the form of a spray. The spray typically includes the composition comprising the one or more lactones and a cosmetically acceptable carrier. In some embodiments, the carrier is water or a water and alcohol mixture. The spray formulation optionally includes an antioxidant, sunscreen agent, vitamin, protein, peptide, plant extract, humectant, oil, emollient, lubricant, thickener, hair conditioning agent, polymer, and/or surfactant. Preferably, the spray formulation includes a preservative. In some embodiments, the formulation includes a fragrance. In some cases, the compositions described herein include a surfactant. In some cases, the compositions described herein contain water, fragrance, a preservative, and one or more lactones. In some cases, the compositions described herein contain water, fragrance, a preservative, and one or more lactones. In some cases, the composition comprising one or more lactones contains water, a preservative, fragrance, the one or more lactones, and an anti-static agent. In some cases, the compositions described herein contain water, a preservative, fragrance, the one or more lactones, and a hair conditioning agent. In some cases, the compositions described herein contain water, a preservative, fragrance, the one or more lactones, and a surfactant.

The hair spray formulations may be dispensed from containers that include aerosol dispensers or pump spray dispensers. Such dispensers are known in the art and are commercially available from a variety of manufacturers.

When the hair spray formulation is dispensed from a pressurized aerosol container, a propellant may be used to force the composition out of the container. Suitable propellants include, but are not limited to, a liquefiable gas or a halogenated propellant. Examples of suitable propellants include dimethyl ether and hydrocarbon propellants such as propane, n-butane, iso-butane, CFCs, and CFC-replacement propellants. The propellants may be used singly or admixed.

The amount of propellant may range from about 10% to about 60% by weight of the formulation. The propellant may be separated from the hair repair formulation as in a two compartment container. Other suitable aerosol dispensers are those characterized by the propellant being compressed air, which can be filled into the dispenser using a pump or equivalent device prior to use. Conventional non-aerosol pump spray dispensers, i.e., atomizers, may also be used to apply the hair strengthening formulation to the hair.

ii. Conditioners

The compositions disclosed herein for treatment of hair may be in the form of a conditioner. The conditioner typically includes the composition comprising the one or more lactones in a suitable carrier. Additionally, the conditioner may include cationic polymers derived from polysaccharides, for example cationic cellulose derivatives, cationic starch derivatives, cationic guar derivatives and cationic locust bean gum derivatives, synthetic cationic polymers, mixtures or combinations of these agents. The formulation may comprise other synthetic or natural polymers or polymers derived from biological preparation processes, which are functionalized, where appropriate, for example with cationic or neutral groups. These polymers may have a stabilizing or strengthening action on the compositions, and/or a conditioning action (deposition on the surface of the skin or the hair).

iii. Creams

The compositions disclosed herein for treatment of hair may be in the form of a cream. The cream typically includes one or more lactones in a suitable carrier. The one or more lacatones may be included in any suitable concentration. Typical concentrations of the one or more lactones in the cream range from small amounts such as approximately about 0.01% (wt), at least 0.1% (wt), to large amounts, such as up to about 50% (wt).

Implementation of the present disclosure is provided by way of the following examples. The examples serve to illustrate the technology without being limiting in nature.

Examples

Normal bleached hair swatches (from IHIP, about 1.5 grams) were treated and evaluated as set forth below.
Pre-Color Treatment: Normal bleached hair swatches were treated with a pre-color treatment of either a 50 wt. % calcium chloride dihydrate solution or 40 wt. % trisodium citrate solution (0.5 g solution/1 g of hair).
Color Treatment Only: Hair swatches were colored using a commercial hair coloring product (1 g color creme/1.5 g developer/1 g hair) for 30 minutes to give the hair an intense auburn color.
In-Color Treatment: Hair swatches were colored using a commercial color product that was combined with either a salt of a hydroxy-polycarboxylic acid (trisodium citrate) or an alkaline earth metal salt (calcium chloride) (1 g solution of 50 wt. % calcium chloride dihydrate or 40 wt. % trisodium citrate/1 g color creme/1.5 g developer/1 g hair) for 30 minutes to give the hair an intense auburn color.
Post-Color Treatment: The hair swatches were treated with a post-color treatment of either a 50 wt. % calcium chloride dihydrate or a 40 wt. % trisodium citrate (0.5 g solution/1 g of hair). The treated hair was allowed to stand at room temperature overnight.
Hair Shampooing: The treated hair swatches were washed with an anionic shampoo (12% SLES, pH=5.5) 10 times. The hair swatch were blown dry after each shampoo.
Color Assessment: The L* and a* values of the hair swatches were obtained before and after 10 shampoos. The higher the L* and the a* values, the lighter and redder the hair, respectively. The L*a*b* colorimetric system is a colorimetric system that assigns each color to a position in a spherical color space. In this color space, the brightness is represented by a position in the ordinate (z-axis) direction, the hue is represented by a position in the circumferential direction, and the chroma is represented by a distance from the center axis. The position on the ordinate (z-axis) representing brightness is designated by L*, and the L* value changes from 0 corresponding to black to 100 corresponding to white. The positive direction of the x-axis corresponds to a red direction, the positive direction of the y-axis corresponds to a yellow direction, the negative direction of the x-axis corresponds to a green direction, the negative direction of the y-axis corresponds to a blue direction, and the position on the x-axis is designated by a* of which value changes from −60 to +60 and the position on the y-axis is designated by b* of which value changes from −60 to +60. The hue and chroma are represented by a* value and b* value, respectively.

The results of the treatments described above are provided below in tables 1-6.

TABLE 1

Pre-color treatment (using salt of hydroxy-polycarboxylic acid) + In-Color Treatment (using alkaline earth metal salt)

| | L-Value | | a-Value | |
|---|---|---|---|---|
| Treatment | Before | After | Before | After |
| No Treatment (control)* | 27.5 | 34.9 | 16.8 | 15.4 |
| Pre-color treatment using salt of hydroxy-polycarboxylic acid (trisodium citrate) | 27.9 | 36.0 | 18.8 | 16.5 |
| In-color treatment using alkaline earth metal salt (CaCl$_2$) | 24.1 | 33.3 | 12.9 | 17.1 |
| Pre-color treatment using salt of hydroxy-polycarboxylic acid (trisodium citrate) and in-color treatment using alkaline earth metal salt (CaCl$_2$) | 24.4 | 32.8 | 14.0 | 17.3 |

*Colored hair without treatment with a salt of hydroxy-polycarboxylic acid or treatment with an alkaline earth metal salt.

TABLE 2

Pre-color treatment (using alkaline earth metal salt) + In-Color Treatment (using salt of hydroxy-polycarboxylic acid)

| | L-Value | | a-Value | |
|---|---|---|---|---|
| Treatment | Before | After | Before | After |
| No Treatment (control)* | 27.6 | 34.3 | 17.2 | 16.2 |
| Pre-color treatment using alkaline earth metal salt (CaCl$_2$) | 24.4 | 32.4 | 13.5 | 16.9 |
| In-color treatment using salt of hydroxy-polycarboxylic acid (trisodium citrate) | 26.2 | 36.0 | 18.0 | 16.6 |
| Pre-color treatment using using alkaline earth metal salt (CaCl$_2$) and in-color treatment using salt of hydroxy-polycarboxylic acid (trisodium citrate) | 24.7 | 32.0 | 14.8 | 17.4 |

*Colored hair without treatment with a salt of hydroxy-polycarboxylic acid or treatment with an alkaline earth metal salt.

TABLE 3

Pre-color treatment (using salt of hydroxy-polycarboxylic acid) + Post-Color Treatment (using alkaline earth metal salt)

| | L-Value | | a-Value | |
|---|---|---|---|---|
| Treatment | Before | After | Before | After |
| No Treatment (control)* | 28.0 | 33.4 | 15.4 | 16.5 |
| Pre-color treatment using salt of hydroxy-polycarboxylic acid (trisodium citrate) | 27.5 | 33.3 | 16.4 | 17.2 |
| Post-color treatment using alkaline earth metal salt (CaCl$_2$) | 28.4 | 35.0 | 17.1 | 16.6 |

TABLE 3-continued

Pre-color treatment (using salt of hydroxy-polycarboxylic acid) +
Post-Color Treatment (using alkaline earth metal salt)

|  | L-Value | | a-Value | |
|---|---|---|---|---|
| Treatment | Before | After | Before | After |
| Pre-color treatment using salt of hydroxy-polycarboxylic acid (trisodium citrate) and post-color treatment using alkaline earth metal salt (CaCl$_2$) | 25.3 | 31.5 | 15.9 | 17.6 |

*Colored hair without treatment with a salt of hydroxy-polycarboxylic acid or treatment with an alkaline earth metal salt.

TABLE 4

Pre-color treatment (using alkaline earth metal salt) +
Post-color treatment (using salt of hydroxy-polycarboxylic acid)

|  | L-Value | | a-Value | |
|---|---|---|---|---|
| Treatment | Before | After | Before | After |
| No Treatment (control)* | 28.0 | 34.9 | 16.7 | 15.9 |
| Pre-color treatment using alkaline earth metal salt (CaCl$_2$) | 24.6 | 34.7 | 10.9 | 16.5 |
| Post-color treatment using salt of hydroxy-polycarboxylic acid (trisodium citrate) | 28.1 | 32.7 | 16.1 | 17.0 |
| Pre-color treatment using using alkaline earth metal salt (CaCl$_2$) and post-color treatment using salt of hydroxy-polycarboxylic acid (trisodium citrate) | 23.8 | 31.7 | 10.6 | 17.9 |

*Colored hair without treatment with a salt of hydroxy-polycarboxylic acid or treatment with an alkaline earth metal salt.

TABLE 5

In-Color Treatment (using salt of hydroxy-polycarboxylic acid) +
Post-Color Treatment (using alkaline earth metal salt)

|  | L-Value | | a-Value | |
|---|---|---|---|---|
| Treatment | Before | After | Before | After |
| No Treatment (control)* | 28.2 | 35.6 | 16.8 | 15.7 |
| In-color treatment using salt of hydroxy-polycarboxylic acid (trisodium citrate) | 26.4 | 35.0 | 17.7 | 17.6 |
| Post-color treatment using alkaline earth metal salt (CaCl$_2$) | 27.7 | 32.7 | 17.4 | 17.4 |
| In-color treatment using salt of hydroxy-polycarboxylic acid (trisodium citrate) and post-color treatment using alkaline earth metal salt (CaCl$_2$) | 27.2 | 30.6 | 17.7 | 18.7 |

*Colored hair without treatment with a salt of hydroxy-polycarboxylic acid or treatment with an alkaline earth metal salt.

TABLE 6

In-Color treatment (using alkaline earth metal salt) +
Post-color treatment (using salt of hydroxy-polycarboxylic acid)

|  | L-Value | | a-Value | |
|---|---|---|---|---|
| Treatment | Before | After | Before | After |
| No Treatment (control)* | 29.0 | 34.7 | 17.8 | 15.6 |
| In-color treatment using alkaline earth metal salt (CaCl$_2$) | 24.2 | 33.9 | 11.6 | 18.4 |
| Post-color treatment using salt of hydroxy-polycarboxylic acid (trisodium citrate) | 28.6 | 34.9 | 17.4 | 16.5 |

TABLE 6-continued

In-Color treatment (using alkaline earth metal salt) +
Post-color treatment (using salt of hydroxy-polycarboxylic acid)

|  | L-Value | | a-Value | |
|---|---|---|---|---|
| Treatment | Before | After | Before | After |
| In-color treatment using alkaline earth metal salt (CaCl$_2$) and post-color treatment using salt of hydroxy-polycarboxylic acid (trisodium citrate) | 26.0 | 33.4 | 14.2 | 18.5 |

*Colored hair without treatment with a salt of hydroxy-polycarboxylic acid or treatment with an alkaline earth metal salt.

As shown by the data in the tables above, the treatments with trisodium citrate provided better initial red color deposition but the color faded after 10 shampoos. The treatments with calcium chloride provided good initial darkness, but the redness lightened after 10 shampoos. Treatments with both the trisodium citrate and the calcium chloride provided the best results; the combination resulted in excellent initial color deposition that was retained after 10 shampoos. Both the darkness and the red hue were unexpectedly retained after 10 shampoos.

The terms "a," "an," and "the" are understood to encompass the plural as well as the singular.

The expression "at least one" means "one or more" and vice versa, and thus includes individual components as well as mixtures/combinations.

The term "about" when referring to a value, is meant specifically that a measurement can be rounded to the value using a standard convention for rounding numbers. For example, "about 1.5" is 1.45 to 1.54. All values set forth herein can be modified with the term "about," if desired to impart the meaning above, or recited without the term in order to have their ordinary meaning, regardless of whether the term "about" is specifically set forth (or is absent) in conjunction with any particular value in the specification.

When referring to "compositions described herein," all types of compositions are intended unless specifically described otherwise. The "compositions disclosed herein" include the compositions comprising one or more reducing agent, the composition comprising one or more lactones, to oxidizing compositions, etc.

All ranges and values disclosed herein are inclusive and combinable. For examples, any value or point described herein that falls within a range described herein can serve as a minimum or maximum value to derive a sub-range, etc.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A method for artificially coloring hair and inhibiting the coloring from fading, the method comprising:
    (a) treating hair with a pre-color treatment composition comprising about 1 wt. % to about 75 wt. % of one or more alkaline earth metal salts or about 1 wt. % to about 75 wt. % of one or more salts of a hydroxy-polycarboxylic acid, wherein hydroxy-polycarboxylic acid has the formula:

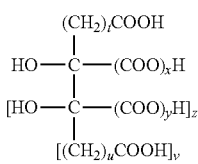

wherein, x and y are independently 0 or 1; and
t, u, v, and z are independently 0 to 3; and
(b) treating the hair with a coloring composition comprising about 1 wt. % to about 50 wt. % of the one or more alkaline earth metal salts or about 1 wt. % to about 50 wt. % of the one or more salts of a hydroxy-polycarboxylic acid;
provided that when the one or more alkaline earth metal salts is used in the pre-color treatment composition, the one or more salts of the hydroxy-polycarboxylic acid is used in the coloring composition, and vice versa.

2. The method of claim 1, wherein the one or more salts of the hydroxy-polycarboxylic acid are salts of citric acid, tartaric acid, malic acid, 2-hydroxy malonic acid, 2-hydroxyl n-butyl 1,2,4-tricarboxylic acid, glucaric acid, and/or 2-hydroxy n-butyl 1,3,4-tricarboxylic acid.

3. The method of claim 1, wherein the one or more salts of the hydroxy-polycarboxylic acid comprises trisodium citrate.

4. The method of claim 1, wherein the one or more alkaline earth metal salts are selected from the group consisting of magnesium chloride, magnesium sulfate, magnesium nitrate, magnesium acetate, magnesium carbonate and hydrogencarbonate, magnesium phosphate, magnesium oxalate, calcium chloride, calcium nitrate, calcium acetate, calcium hydrogen carbonate, strontium chloride, strontium nitrate, barium chloride, and barium nitrate.

5. The method of claim 1, wherein the pre-treatment composition of (a) is applied to the hair and allowed to remain on the hair for about 1 minute to about 1 hour at a temperature of about 25° C. to about 45° C. before treatment with the coloring composition of (b).

6. A kit comprising both a pre-color treatment composition and a coloring composition, as defined in claim 1.

7. A method for artificially coloring hair and inhibiting the coloring from fading, the method comprising:
(a) treating hair with a pre-color treatment composition comprising about 1 wt. % to about 75 wt. % of one or more alkaline earth metal salts or about 1 wt. % to about 75 wt. % of one or more salts of a hydroxy-polycarboxylic acid of the formula

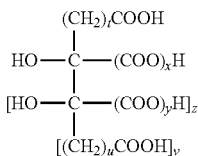

wherein, x and y are independently 0 or 1; and
t, u, v, and z are independently 0 to 3; and
(b) treating the hair with a coloring composition; and
(c) treating the hair with a post-color treatment composition comprising about 1 wt. % to about 75 wt. % of the one or more alkaline earth metal salts or about 1 wt. % to about 75 wt. % of the one or more salts of a hydroxy-polycarboxylic acid;
provided that when the one or more alkaline earth metal salts is used in the pre-color treatment composition, the one or more salts of the hydroxy-polycarboxylic acid is used in the post-color treatment compositions, and vice versa.

8. The method of claim 7, wherein the one or more alkaline earth metal salts are selected from the group consisting of magnesium chloride, magnesium sulfate, magnesium nitrate, magnesium acetate, magnesium carbonate and hydrogencarbonate, magnesium phosphate, magnesium oxalate, calcium chloride, calcium nitrate, calcium acetate, calcium hydrogen carbonate, strontium chloride, strontium nitrate, barium chloride, and barium nitrate.

9. The method of claim 7, wherein the one or more alkaline earth metal salts of (a) comprises calcium chloride.

10. The method of claim 7, wherein the one or more salts of the hydroxy-polycarboxylic acid are salts of citric acid, tartaric acid, malic acid, 2-hydroxy malonic acid, 2-hydroxyl n-butyl 1,2,4-tricarboxylic acid, glucaric acid, and/or 2-hydroxy n-butyl 1,3,4-tricarboxylic acid.

11. The method of claim 7, wherein the pre-treatment composition of (a) is applied to the hair and allowed to remain on the hair for about 1 minute to about 1 hour at a temperature of about 25° C. to about 45° C. before treatment with the coloring composition of (b); and the post-treatment composition of (c) is applied to the hair within about 1 hour of the hair being artificially colored and is allowed to remain on the hair for about 1 minute to about 1 hour at a temperature of about 20° C. to about 45° C.

12. A kit comprising both a pre-color treatment composition and a coloring composition, as defined in claim 7.

13. A method for artificially coloring hair and inhibiting the coloring from fading, the method comprising:
(a) treating the hair with a coloring composition comprising about 1 wt. % to about 50 wt. % of one or more alkaline earth metal salts or about 1 wt. % to about 50 wt. % of one or more salts of a hydroxy-polycarboxylic acid, wherein hydroxy-polycarboxylic acid has the formula:

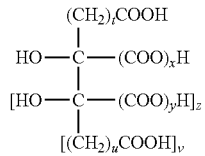

wherein, x and y are independently 0 or 1; and
t, u, v, and z are independently 0 to 3; and
(b) treating the hair with a post-color treatment composition comprising about 1 wt. % to about 75 wt. % of the one or more alkaline earth metal salts or about 1 wt. % to about 75 wt. % of the one or more salts of a hydroxy-polycarboxylic acid;
provided that when the one or more alkaline earth metal salts is used in the coloring composition, the one or more salts of the hydroxy-polycarboxylic acid is used in the post-color treatment composition, and vice versa.

14. The method of claim 13, wherein the one or more alkaline earth metal salts of are selected from the group consisting of magnesium chloride, magnesium sulfate, magnesium nitrate, magnesium acetate, magnesium carbonate and hydrogencarbonate, magnesium phosphate, magnesium oxalate, calcium chloride, calcium nitrate, calcium acetate, calcium hydrogen carbonate, strontium chloride, strontium nitrate, barium chloride, and barium nitrate.

15. The method of claim 13, wherein post-treatment composition of (b) is applied to the hair within about 1 hour of the hair being artificially colored and is allowed to remain on the hair for about 1 minute to about 1 hour at a temperature of about 20° C. to about 45° C.

16. The method of claim 13, wherein the one or more salts of the hydroxy-polycarboxylic acid are salts of citric acid, tartaric acid, malic acid, 2-hydroxy malonic acid, 2-hydroxyl n-butyl 1,2,4-tricarboxylic acid, glucaric acid, and/or 2-hydroxy n-butyl 1,3,4-tricarboxylic acid.

17. The method of claim 13, wherein the one or more salts of the hydroxy-polycarboxylic acid comprises trisodium citrate.

18. A kit comprising both a pre-color treatment composition and a coloring composition, as defined in claim 13.

19. A method for artificially coloring hair and inhibiting the color from fading, the method comprising:
treating the hair with a coloring composition;
treating the hair one or more alkaline earth metal salts; and
treating the hair with one or more salts of a hydroxy-polycarboxylic acid,
wherein hydroxy-polycarboxylic acid has the formula:

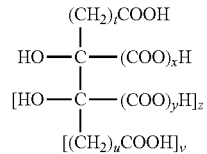

wherein, x and y are independently 0 or 1; and
t, u, v, and z are independently 0 to 3;
wherein the one or more alkaline earth metal salts and the one or more hydroxyl-polycarboxylic acids are applied to the hair separately; and wherein the one or more earth metal salts or the one or more hydroxyl-polycarboxylic acids applied to the hair as a pre-color treatment, an in-color treatment, or a post-color treatment.

* * * * *